(12) United States Patent
Adam et al.

(10) Patent No.: US 9,334,202 B2
(45) Date of Patent: *May 10, 2016

(54) PROCESS TO MAKE PROPYLENE FROM ISOBUTANOL BY DEHYDRATION AND SUBSEQUENT CRACKING

(71) Applicant: TOTAL RESEARCH & TECHNOLOGY FELUY, Seneffe (BE)

(72) Inventors: Cindy Adam, Wierde (BE); Delphine Minoux, Nivelles (BE); Nikolai Nesterenko, Nivelles (BE); Sander Van Donk, Sainte-Adresse (FR); Jean-Pierre Dath, Beloeil (BE)

(73) Assignee: Total Research & Technology Feluy, Seneffe (BE)

( * ) Notice: Subject to any disclaimer, the term of this patent is extended or adjusted under 35 U.S.C. 154(b) by 0 days.

This patent is subject to a terminal disclaimer.

(21) Appl. No.: 14/710,782

(22) Filed: May 13, 2015

(65) Prior Publication Data

US 2015/0239801 A1  Aug. 27, 2015

Related U.S. Application Data

(63) Continuation of application No. 13/813,107, filed as application No. PCT/EP2011/061581 on Jul. 8, 2011, now Pat. No. 9,079,813.

(30) Foreign Application Priority Data

Aug. 3, 2010 (EP) .................................... 10171668

(51) Int. Cl.

| C07C 1/24 | (2006.01) |
|---|---|
| C07C 4/06 | (2006.01) |
| C10G 3/00 | (2006.01) |
| C12P 5/02 | (2006.01) |
| C12P 7/16 | (2006.01) |
| B01J 21/04 | (2006.01) |
| B01J 29/40 | (2006.01) |
| B01J 29/65 | (2006.01) |

(52) U.S. Cl.
CPC ... *C07C 1/24* (2013.01); *C07C 4/06* (2013.01); *C10G 3/44* (2013.01); *C10G 3/49* (2013.01); *C12P 5/026* (2013.01); *C12P 7/16* (2013.01); *B01J 21/04* (2013.01); *B01J 29/40* (2013.01); *B01J 29/65* (2013.01); *C07C 2521/04* (2013.01); *C07C 2529/40* (2013.01); *C07C 2529/65* (2013.01); *C07C 2529/85* (2013.01); *C10G 2300/1014* (2013.01); *C10G 2300/201* (2013.01); *C10G 2300/4081* (2013.01); *C10G 2400/20* (2013.01); *C10G 2400/22* (2013.01); *Y02E 50/10* (2013.01); *Y02P 20/52* (2015.11); *Y02P 30/20* (2015.11); *Y02P 30/42* (2015.11)

(58) Field of Classification Search
CPC ............ C07C 1/22; C07C 1/24; C07C 11/08; C07C 11/06
USPC .................................. 585/638, 639, 640, 641
See application file for complete search history.

(56) References Cited

U.S. PATENT DOCUMENTS

| 4,621,161 A * | 11/1986 | Shihabi ........................ 585/408 |
|---|---|---|
| 4,695,560 A | 9/1987 | Gattuso et al. |
| 6,797,851 B2 * | 9/2004 | Martens .................... C07C 1/20 585/639 |
| 2005/0096492 A1 * | 5/2005 | Dath ...................... C10G 11/16 585/653 |
| 2010/0041930 A1 * | 2/2010 | Gartside et al. ............... 585/314 |
| 2010/0249476 A1 * | 9/2010 | Lefenfeld et al. ............. 585/435 |
| 2011/0282117 A1 * | 11/2011 | Cross et al. .................... 585/254 |

OTHER PUBLICATIONS

Taylor et al. Dehydration of Fermented Isobutanol for the Production of Renewable Chemicals and Fuels. Top Catal (2010) 53: 1224-1230.*

* cited by examiner

*Primary Examiner* — In Suk Bullock
*Assistant Examiner* — Sharon Pregler
(74) *Attorney, Agent, or Firm* — Albert Shung

(57) ABSTRACT

A process for conversion of isobutanol to make propylene includes dehydrating isobutanol to produce butenes. The process includes cracking the butenes to produce propylene.

22 Claims, 1 Drawing Sheet

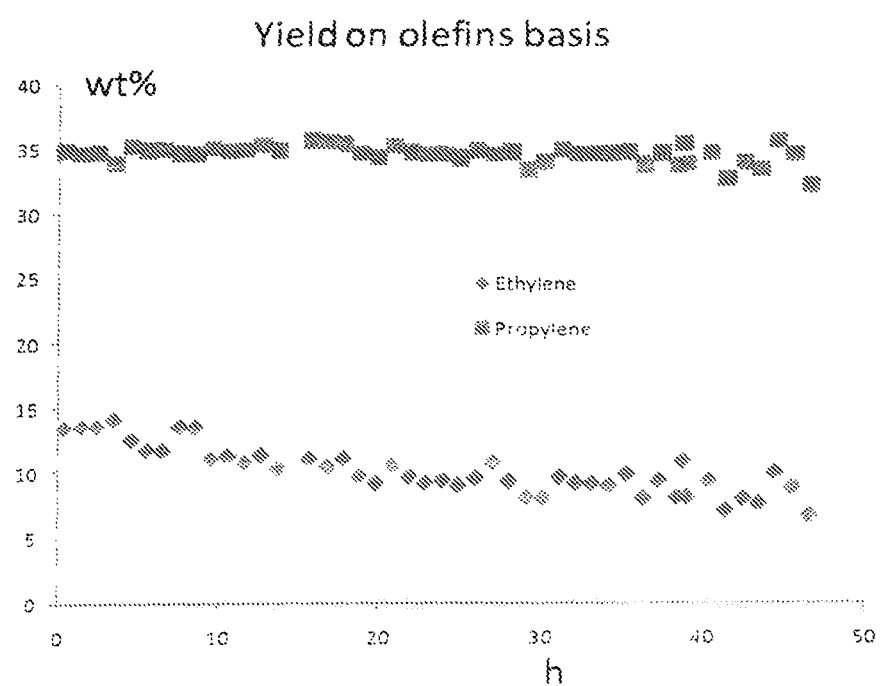

PROCESS TO MAKE PROPYLENE FROM ISOBUTANOL BY DEHYDRATION AND SUBSEQUENT CRACKING

CROSS-REFERENCE TO RELATED APPLICATIONS

This application is a Continuation of U.S. patent application Ser. No. 13/813,107, filed on Apr. 5, 2013, which is a National Stage Entry of PCT/EP2011/061581, filed on Jul. 8, 2011, which claims priority from EP 10171668.6, filed on Aug. 3, 2010.

FIELD OF THE INVENTION

The present invention relates to the transformation of isobutanol-containing feedstock to an olefin stream comprising propylene by combined process including dehydration step followed by cracking step. The limited supply and increasing cost of crude oil has prompted the search for alternative processes for producing hydrocarbon products such as propylene. i-Butanol can be obtained by fermentation of carbohydrates coming from the biomass, via the syngas route or base-catalysed Guerbet condensation. Made up of organic matter from living organisms, biomass is the world's leading renewable energy source.

BACKGROUND OF THE INVENTION

The bio-ethanol is one of the most relevant sources of bio-carbon today. This platform molecule available today at a price of its calorific value is venturing out of fuel application being used as precursor for base chemicals. While the ethylene can easily produced by dehydration from ethanol, the direct conversion of ethanol to propylene is problematic due to very low yield.

One step process provides a wide diversity in the formed products obtained in minor amounts which monetizing is not very obvious. Multistep process which includes ethanol dehydration to ethylene, offers better overall selectivity to propylene. However, the obtained ethylene has to be first dimerized to butene or oligomerized to be further reacted via metathesis or via cracking in OCP (olefin cracking process) reactor. The complexity of the multistep process increases significantly the manufacturing costs of bio-propylene.

The way to produce bio-propylene can be accomplished by employing a new concept: using isobutanol as a platform molecule. Of the described routes towards isobutanol, the Guerbet condensation, the synthesis gas conversion to alcohols and the 2-keto acid pathway from carbohydrates are routes that can use biomass as primary feedstock. The fermentation of sugar as well as a syn-gas conversion may result directly to formation of heavy alcohols (C3+), in particular i-butanol, which is often an abundant product (Applied Catalysis A, general, 186, p. 407, 1999 and Chemiker Zeitung, 106, p. 249, 1982).

Gasification of biomass results in synthesis gas that can be converted after purification into methanol, ethanol, propanol or directly into isobutanol. In addition, methanol and ethanol or propanol resourced from biomass can be further condensed to isobutanol. The base-catalysed Guerbet condensation of methanol with ethanol and/or propanol increases the concentration of i-butanol in the alcohol fraction and in particular in C3+ heavy alcohols fraction (J. of Molecular Catalysis A: Chemical 200, 137, 2003 and Applied Biochemistry and Biotechnology, 113-116, p. 913, 2004).

Isobutanol (2-methyl-1-propanol) has historically found limited applications and its use resembles that of 1-butanol. It has been used as solvent, diluent, wetting agent, cleaner additive and as additive for inks and polymers. Recently, isobutanol has gained interest as fuel or fuel component as it exhibits a high octane number (Blend Octane R+M/2 is 102-103) and a low vapor pressure (RVP is 3.8-5.2 psi).

Isobutanol is often considered as a byproduct of the industrial production of 1-butanol (Ullmann's encyclopedia of industrial chemistry, 6$^{th}$ edition, 2002). It is produced from propylene via hydroformylation in the oxo-process (Rh-based catalyst) or via carbonylation in the Reppe-process (Co-based catalyst). Hydroformylation or carbonylation makes n-butanal and iso-butanal in ratios going from 92/8 to 75/25. To obtain isobutanol, the iso-butanal is hydrogenated over a metal catalyst.

Recently, new biochemical routes have been developed to produce selectively isobutanol from carbohydrates. The new strategy uses the highly active amino acid biosynthetic pathway of microorganisms and diverts its 2-keto acid intermediates for alcohol synthesis. 2-Keto acids are intermediates in amino acid biosynthesis pathways. These metabolites can be converted to aldehydes by 2-keto-acid decarboxylases (KDCs) and then to alcohols by alcohol dehydrogenases (ADHs). Two non-native steps are required to produce alcohols by shunting intermediates from amino acid biosynthesis pathways to alcohol production (Nature, 451, p. 86, 2008 and US patent 2008/0261230). Recombinant microorganisms are required to enhance the flux of carbon towards the synthesis of 2-keto-acids. In the valine biosynthesis 2-ketoisovalerate is an intermediate. Glycolyse of carbohydrates results in pyruvate that is converted into acetolactate by acetolactate synthase. 2,4-dihydroxyisovalerate is formed out of acetolactate, catalysed by isomeroreductase. A dehydratase converts the 2,4-dihydroxyisovalerate into 2-keto-isovalerate. In the next step, a keto acid decarboxylase makes isobutyraldehyde from 2-keto-isovalerate. The last step is the hydrogenation of isobutyraldehyde by a dehydrogenase into isobutanol.

The direct 2-keto acid pathway can produce isobutanol from carbohydrates that are isolated from biomass. Simple carbohydrates can be obtained from plants like sugar cane, sugar beet. More complex carbohydrates can be obtained from plants like maize, wheat and other grain bearing plants. Even more complex carbohydrates can be isolated from substantially any biomass, through unlocking of cellulose and hemicellulose from lignocelluloses.

The isobutanol can be dehydrated to corresponding mixture of olefins containing the same number of atoms. Dehydration of butanols has been described on alumina-type catalysts (Applied Catalysis A, General, 214, p. 251-257, 2001). Both double-bond shift and skeletal isomerisation has been obtained at very low space velocity (or very long reaction time) corresponding to a GHSV (Gas Hourly Space Velocity=ratio of feed rate (gram/h) to weight of catalyst (ml)) of less than 1 gram·ml$^{-1}$·h$^{-1}$. The dehydration reactions of alcohols to produce alkenes with the same number of carbons have been known for a long time (J. Catal. 7, p. 163, 1967 and J. Am. Chem. Soc. 83, p. 2847, 1961). Many available solid acid catalysts can be used for alcohol dehydration (Stud. Surf. Sci. Catal. 51, p. 260, 1989), the European patent EP0150832, Bulletin of the Chemical Society of Japan, vol 47(2), 424-429 (1974). However, γ-aluminas are the most commonly used, especially for the longer chain alcohols (with three and more carbon atoms). This is because catalysts with stronger acidity, such as the silica-aluminas, molecular sieves, zeolites or resin catalysts can promote double-bond shift, skeletal isomerization and other olefin interconversion reactions.

The primary product of the acid-catalysed dehydration of isobutanol is isobutene and water:

So, the dehydration may result in substantially pure isobutene stream or in blended olefinic stream reach in butenes if a secondary reaction occurs on the catalyst.

EP 2070896 A1 describes the dehydration of 1-butanol on a porous crystalline aluminosilicate (TON type) in the hydrogen form. At 500° C. the products are in wt %:

| | |
|---|---|
| propylene | 10.76 |
| trans-butene-2 | 16.99 |
| butene-1 | 13.49 |
| isobutene | 31.30 |
| cis-butene-2 | 13.33 |

The production of light olefins (ethylene and propylene) from a mixed alcohol feedstock in an oxygenates to olefins process has been described in the U.S. Pat. No. 7,288,689. Said patent provides various processes for producing C1 to C4 alcohols, optionally in a mixed alcohol stream, and optionally converting the alcohols to light olefins. In one embodiment, it includes directing a first portion of a syngas stream to a methanol synthesis zone wherein methanol is synthesized. A second portion of the syngas stream is directed to a fuel alcohol synthesis zone wherein fuel alcohol is synthesized. The methanol and at least a portion of the fuel alcohol are directed to an oxygenate to olefin reaction system for conversion thereof to ethylene and propylene. In this prior art "fuel alcohol" means an alcohol-containing composition comprising ethanol, one or more C3 alcohols, one or more C4 alcohols and optionally one or more C5+ alcohols. At col 21 lines 14+ is mentioned " . . . Additionally or alternatively, the fuel alcohol-containing stream comprises one or more C4 alcohols, preferably on the order of from about 0.1 to about 20 weight percent C4 alcohols, preferably from about I to about 10 weight percent C4 alcohols, and most preferably from about 2 to about 5 weight percent C4 alcohols, based on the total weight of the fuel alcohol-containing stream. The fuel alcohol-containing stream preferably comprises at least about 5 weight percent C3-C4 alcohols, more preferably at least about 10 weight percent C3-C4 alcohols, and most preferably at least about 15 weight percent C3-C4 alcohols . . . ". Preferably, the molecular sieve catalyst composition comprises a small pore zeolite or a molecular sieve selected from the group consisting of: MeAPSO, SAPO-5, SAPO-8, SAPO-11, SAPO-16, SAPO-17, SAPO-18, SAPO-20, SAPO-031, SAPO-34, SAPO-35, SAPO-36, SAPO-37, SAPO-40, SAPO-41, SAPO-42, SAPO-44, SAPO-47, SAPO-56, AEI/CHA intergrowths, metal containing forms thereof, intergrown forms thereof, and mixtures thereof.

U.S. Pat. No. 6,768,037 describes a process for upgrading a Fischer-Tropsch product comprising paraffins, oxygenates (alcohols), and C6+ olefins. The process includes contacting the Fischer-Tropsch product with an acidic olefin cracking catalyst (ZSM-5) to convert the oxygenates and C6+ olefins to form light olefins. The contacting conditions include a temperature in the range of about 500° F. to 850° F., a pressure below 1000 psig, and a liquid hourly space velocity in the range of from about 1 to 20 hr$^{-1}$. The process further includes recovering the Fischer-Tropsch product comprising unreacted paraffins, and recovering the light olefins. At col 6 lines 16+ is mentioned " . . . . The product from a Fischer-Tropsch process contains predominantly paraffins; however, it may also contain C6+ olefins, oxygenates, and heteroatom impurities. The most abundant oxygenates in Fischer-Tropsch products are alcohols, and mostly primary linear alcohols. Less abundant types of oxygenates in Fischer-Tropsch products include other alcohol types such as secondary alcohols, acids, esters, aldehydes, and ketones . . . ".

WO 2007-149399 relates to a process for making at least one butene comprising contacting a reactant comprising isobutanol and at least about 5% water (by weight relative to the weight of the water plus isobutanol) with at least one acid catalyst at a temperature of about 50° C. to about 450° C. and a pressure from about 0.1 MPa to about 20.7 MPa to produce a reaction product comprising said at least one butene, and recovering said at least one butene from said reaction product to obtain at least one recovered butene. At page 3 is mentioned " . . . The term "butene" includes 1-butene, isobutene, and/or cis and trans 2-butene . . . ". All the examples are made between 120° C. and 200° C.

U.S. Pat. No. 4,698,452 relates to a novel process for the conversion of ethanol or its mixtures with light alcohols and optionally water into hydrocarbons with specific and unusual selectivity towards ethylene. More particularly, it relates to the use of ZSM-5 zeolite based catalysts into which Zn alone or Zn and Mn are incorporated. The preferred reaction conditions used in the experiments are as follows: teimperature=300° C.-450° C. (most preferred 400° C.); catalyst weight=4 g; total pressure=1 atm; alcohol or aqueous ethanol pressure=0.9 atm; inert gas (stripping gas)=nitrogen; weight hourly space velocity (W.H.S.V.)=2.4 h-1; duration of a run=4 hours. At table 3 dehydration of isobutanol has been made on ZSM-5 (Zn—Mn) and produces paraffins C1-C4, ethylene, propylene, butenes, aromatics and aliphatics.

It has now been discovered that isobutanol or a mixture of isobutanol and other alcohols can be dehydrated in first reaction zone or low temperature reaction zone to produce substantially butenes and other olefins and said butenes and other olefins further cracked in a second reaction zone or high temperature zone (also referred as OCP meaning Olefins Cracking Process) to produce ethylene and essentially propylene.

OCP reaction occurs typically at high temperature, higher than 500° C. There are zeolitic type of catalyst used in that process which may suffer from steam if any water precursors are presented in the feedstock. This limits the processing in OCP reactor to the bio-types of feedstock which are typically rich in oxygenates. Optionally water present in the OCP feedstock is removed in whole or in part.

The heavy alcohols can be selectively dehydrated in a low temperature reaction zone (dehydration zone) to corresponding mixture of olefins containing substantially the same number of atom of carbon as a parent oxygenates. The water fraction can be easy separated from the hydrocarbon effluent before the olefins cracking zone providing the co-feed very much similar to the one used typically in OCP process.

The invention proposes a flexible solution to treat the feedstock derived from biomass in existed OCP reactor without provoking any damage for catalyst activity. Each of the processing steps may be tailored to the overall objective of high yield of light olefins containing at least a part of renewable carbon.

BRIEF SUMMARY OF THE INVENTION

The present invention relates to a process for the conversion of an alcohols mixture (A) comprising about 20 w % to 100% isobutanol to make essentially propylene, comprising
a) introducing in a reactor (A) (also called the first reaction zone or low temperature reaction zone) a stream comprising the mixture (A), optionally water, optionally an inert component,
b) contacting said stream with a catalyst (A1) in said reactor (A) at conditions effective to dehydrate:
at least a portion of the isobutanol to essentially butenes,
at least a portion of other alcohols, if any, to essentially olefins other than butene having the same carbon number as the alcohol precursor,
c) recovering from said reactor (A) an effluent comprising:
butenes, optionally olefins other than butene, water, optionally unconverted alcohols of the mixture (A), various hydrocarbons, and the optional inert component of step a),
d) fractionating said effluent of step c) to remove a portion or all the water, unconverted alcohols, optionally the inert component, and optionally the whole or a part of the various hydrocarbons to get a stream (D) comprising essentially olefins and optionally the inert component,
e) introducing at least a part of said stream (D) in an OCP reactor (also called the second reaction zone or high temperature zone),
f) contacting said stream comprising at least a part of (D), optionally in combination with a stream (D1) comprising olefins having 4 carbon atoms or more (C4+ olefins), in said OCP reactor with a catalyst which is selective towards light olefins in the effluent, to produce an effluent with an olefin content of lower molecular weight than that of the feedstock,
g) fractionating said effluent of step f) to produce at least an ethylene stream, a propylene stream and a fraction consisting essentially of hydrocarbons having 4 carbon atoms or more,
optionally recycling ethylene in whole or in part at the inlet of the OCP reactor of step f), or at the inlet of the reactor (A) or at the inlet of both the OCP reactor of step 1) and the reactor (A),
optionally recycling the fraction consisting essentially of hydrocarbons having 4 carbon atoms or more at the inlet of the OCP reactor.

Advantageously at step f) the mixture (D)+(D1) comprises at least 10 wt % of C4+ olefins.

In an embodiment the alcohol feed is subjected to purification to reduce the content in the metal ions, in more particularly in Na, Fe K, Ca and Al.

In a specific embodiment the alcohol mixture (A) comprises 40 to 100 w % of isobutanol.

In a specific embodiment the alcohol mixture (A) comprises 60 to 100 w % of isobutanol.

In a specific embodiment the alcohol mixture (A) comprises 80 to 100 w % of isobutanol.

In a specific embodiment the alcohol mixture (A) comprises essentially isobutanol.

BRIEF DESCRIPTION OF THE DRAWINGS

FIG. depicts a catalyst stability of P-ZSM-5 in olefins cracking.

DETAILED DESCRIPTION OF THE INVENTION

As regards the stream introduced at step a) the inert component is any component provided there is no adverse effect on the catalyst. Because the dehydration is endothermic the inert component can be used to bring energy. By way of examples the inert component is selected among the saturated hydrocarbons having up to 10 carbon atoms, naphtenes, nitrogen and CO2. An example of inert component can be any individual saturated compound, a synthetic mixture of the individual saturated compounds as well as some equilibrated refinery streams like straight naphtha, butanes etc. Advantageously it is a saturated hydrocarbon or a mixture of saturated hydrocarbons having from 3 to 7 carbon atoms, more advantageously having from 4 to 6 carbon atoms and is preferably pentane. The weight proportions of respectively alcohols, water and inert component are, for example, 5-100/0-95/0-95 (the total being 100). The stream (A) can be liquid or gaseous.

The isobutanol-containing feed can be produced by the Guerbet condensation, by the synthesis gas route and by the biochemical routes. The feedstock before subjecting to dehydration can be subjected to a different upgrading procedure including but non-limiting to purification from the metals, separation/extractions of the individual compounds, alcohols interconversion, partial dehydration to ethers, drying etc. The feedstock is essentially free of light alcohols and hydrocarbons.

As regards the reactor (A), it can be a fixed bed reactor, a moving bed reactor or a fluidized bed reactor. A typical fluid bed reactor is one of the FCC type used for fluidized-bed catalytic cracking in the oil refinery. A typical moving bed reactor is of the continuous catalytic reforming type. The dehydration may be performed continuously in a fixed bed reactor configuration using a pair of parallel "swing" reactors. The various preferred catalysts of the present invention have been found to exhibit high stability. This enables the dehydration process to be performed continuously in two parallel "swing" reactors wherein when one reactor is operating, the other reactor is undergoing catalyst regeneration. The catalyst of the present invention also can be regenerated several times.

As regards the pressure in steps a) and b), the pressure of the reactor of step b) can be any pressure but it is more economical to operate at moderate pressure. By way of example the pressure of the reactor ranges from 0.5 to 30 bars absolute (50 kPa to 3 MPa), advantageously from 0.5 to 10 bars absolute (50 kPa to 1 MPa), advantageously from 0.5 to 5 bars absolute (50 kPa to 0.5 MPa), more advantageously from 1.2 to 5 bars absolute (0.12 MPa to 0.5 MPa) and preferably from 1.2 to 4 bars absolute (0.12 MPa to 0.4 MPa). Advantageously, the partial pressure of the alcohols is advantageously lower than 4 bars absolute (0.4 MPa) and more advantageously from 0.5 to 4 bars absolute (0.05 MPa to 0.4 MPa), preferably lower than 3.5 bars absolute (0.35 MPa) and more preferably lower than 2 bars absolute (0.2 MPa).

As regards the temperature in step b), it ranges advantageously from 280° C. to 450° C., more advantageously from 300° C. to 450° C. and preferably from 330° C. to 400° C.

As regards the WHSV of alcohols in step b), it ranges advantageously from 1 to 20 $h^{-1}$, more advantageously from 2 to 20 $h^{-1}$, preferably from 5 to 15 $h^{-1}$, more preferably from 7 to 12 $h^{-1}$.

As regards the catalyst (A1) of step b), it can be any acid catalyst capable to cause the dehydration of alcohols under above said conditions. One can cite molecular sieves, zeolites, modified zeolites (including P-modified zeolites), silico-aluminophosphates, silica-alumina, γ-alumina, transitional aluminas such as α-alumina, β-alumina, γ-alumina, δ-alumina, ε-alumina, κ-alumina, ρ-alumina and modified aluminas. By way of example of modified aluminas one can cite silicated, borated, tungstated, titanated, zirconated or fluorinated alumina, tungstated zirconia, and silica doped with metal oxided.

According to an embodiment the catalyst (A1) is a crystalline Porous Aluminophosphate containing advantageously at least one 10 and/or 12 members ring into the structure.

The porous crystalline aluminophosphate may be one that is comprised of aluminum and phosphorus that are partly substituted by silicon, boron, Ni, Zn, Mg, Mn such as a porous crystalline metalaluminophosphate. The structure of such crystalline porous aluminophosphates may, for example, be those that are identified by codes for zeolites described above as AEL, AFI, AFO or FAU.

The above porous crystalline aluminophosphate is preferably a porous crystalline silicoaluminophosphate. Specifically, SAPO5, and the like having an AFI structure, SAPO41, and the like having an AFO structure, SAPO11, and the like having an AEL structure, structure or SAPO37, and the like having a FAU structure may be mentioned.

According to another specific embodiment, suitable catalysts for the present process is the silicoaluminophosphate molecular sieves, in particular of the AEL group with typical example the SAPO-11 molecular sieve. The SAPO-11 molecular sieve is based on the ALPO-11, having essentially an Al/P ratio of 1 atom/atom. During the synthesis silicon precursor is added and insertion of silicon in the ALPO framework results in an acid site at the surface of the micropores of the 10-membered ring sieve. The silicon content ranges from 0.1 to 10 atom % (Al+P+Si is 100).

Various commercial zeolite products nay be used, or it is possible to use zeolites that have been synthesized by a known method disclosed in e.g. "Verified Synthesis of Zeolitic Materials" ($2^{nd}$ Revised Edition 2001 Elsevier) published by the above IZA.

According to an embodiment the catalyst (A1) is a crystalline silicate containing advantageously at least one 10 members ring into the structure. It is by way of example of the MFI (ZSM-5, silicalite-1, boralite C, TS-1), MEL (ZSM-11, silicalite-2, boralite D, TS-2, SSZ-46), FER (Ferrierite, FU-9, ZSM-35), MTT (ZSM-23), MWW (MCM-22, PSH-3, ITQ-1, MCM-49), TON (ZSM-22, Theta-1, NU-10), EUO (ZSM-50, EU-1), MFS (ZSM-57) and ZSM-48 family of microporous materials consisting of silicon, aluminium, oxygen and optionally boron. Advantageously in said first embodiment the catalyst (A1) is a crystalline silicate or a dealuminated crystalline silicate.

The crystalline silicate can have a ratio Si/Al of at least about 10.

The crystalline silicate, in an embodiment, can have a ratio Si/Al of at least about 100 and is advantageously selected among the MFI and the MEL.

The crystalline silicate and the dealuminated crystalline silicate are essentially in H-form. It means that a minor part (less than about 50%) can carry metallic compensating ions e.g. Na, Mg, Ca, La, Ni, Ce, Zn, Co.

The dealuminated crystalline silicate is advantageously such as about 10% by weight of the aluminium is removed. Such dealumination is advantageously made by a steaming optionally followed by a leaching. Such dealumination is advantageously made by a steaming optionally followed by a leaching.

In another specific embodiment the crystalline silicate catalyst is mixed with a binder, preferably an inorganic binder, and shaped to a desired shape, e.g. pellets. The binder is selected so as to be resistant to the temperature and other conditions employed in the dehydration process of the invention. The binder is an inorganic material selected from clays, silica, metal silicate, metal oxides (such as $ZrO_2$) or gels including mixtures of silica and metal oxides.

According to an embodiment the catalyst (A1) is a P-modified zeolite (Phosphorus-modified zeolite). Said phosphorus modified molecular sieves can be prepared based on MFI, MOR, MEL, clinoptilolite or FER, MWW, TON, EUO, MFS and ZSM-48 family of microporous molecular sieves having an initial Si/Al ratio advantageously between 4 and 500. The P-modified zeolites of this recipe can be obtained based on cheap crystalline silicates with low Si/Al ratio (below 30).

By way of example said P-modified zeolite is made by a process comprising in that order:
  selecting a zeolite (advantageously with Si/Al ratio between 4 and 500) among $H^+$ or $NH_4^+$-form of MFI, MEL, FER, MOR, clinoptilolite, MWW, TON, EUO, MFS and ZSM-48;
  introducing P at conditions effective to introduce advantageously at least 0.05 wt % of P;
  separation of the solid from the liquid if any;
  an optional washing step or an optional drying step or an optional drying step followed by a washing step;
  a calcination step;

The zeolite with low Si/Al ratio has been made previously with or without direct addition of an organic template.

Optionally the process to make said P-modified zeolite comprises the steps of steaming and leaching. The method consists in steaming followed by leaching. It is generally known by the persons in the art that steam treatment of zeolites, results in aluminium that leaves the zeolite framework and resides as aluminiumoxides in and outside the pores of the zeolite. This transformation is known as dealumination of zeolites and this term will be used throughout the text. The treatment of the steamed zeolite with an acid solution results in dissolution of the extra-framework aluminiumoxides. This transformation is known as leaching and this term will be used throughout the text. Then the zeolite is separated, advantageously by filtration, and optionally washed. A drying step can be envisaged between filtering and washing steps. The solution after the washing can be either separated, by way of example, by filtering from the solid or evaporated.

P can be introduced by any means or, by way of example, according to the recipe described in U.S. Pat. No. 3,911,041, U.S. Pat. No. 5,573,990 and U.S. Pat. No. 6,797,851.

The catalyst made of a P-modified zeolite can be the P-modified zeolite itself or it can be the P-modified zeolite formulated into a catalyst by combining with other materials that provide additional hardness or catalytic activity to the finished catalyst product. Advantageously, at least a part of phosphorous is introduced into zeolite before shaping. In a specific embodiment, the formed P-precursor can be further modified with the metals selected from Mg, Ca, La, Ni, Ce, Zn, Co, Ag, Fe, Cu according to the recipe described in WO 09092779 and WO 09092781.

The separation of the liquid from the solid is advantageously made by filtering at a temperature between 0-90° C., centrifugation at a temperature between 0-90° C., evaporation or equivalent.

Optionally, the zeolite can be dried after separation before washing. Advantageously said drying is made at a temperature between 40-600° C., advantageously for 1-10 h. This drying can be processed either in a static condition or in a gas flow. Air, nitrogen or any inert gases can be used.

The washing step can be performed either during the filtering (separation step) with a portion of cold (<40° C.) or hot water (>40 but <90° C.) or the solid can be subjected to a water solution (1 kg of solid/4 liters water solution) and treated under reflux conditions for 0.5-10 h followed by evaporation or filtering.

Final equilibration step is performed advantageously at the temperature 400-800° C. in presence of steam for 0.01-48 h. Advantageously the steam partial pressure is at least 0.1 bars. Air, nitrogen or any inert gases can be fed together with steam.

According to a specific embodiment the phosphorous modified zeolite is made by a process comprising in that order:
- selecting a zeolite (advantageously with Si/Al ratio between 4 and 500, from 4 to 30 in a specific embodiment) among $H^+$ or $NH_4^+$-form of MFI, MEL, FER, MOR, clinoptilolite, MWW, TON, EUO, MFS and ZSM-48;
- steaming at a temperature ranging from 400 to 870° C. for 0.01-200 h;
- leaching with an aqueous acid solution at conditions effective to remove a substantial part of Al from the zeolite;
- introducing P with an aqueous solution containing the source of P at conditions effective to introduce advantageously at least 0.05 wt % of P;
- separation of the solid from the liquid;
- an optional washing step or an optional drying step or an optional drying step followed by a washing step;
- a calcination step.

Optionally between the steaming step and the leaching step there is an intermediate step such as, by way of example, contact with silica powder and drying.

Optionally the leaching and introducing P are made simultaneously by using an acid mixture comprising phosphorus to make the leaching.

Advantageously the selected MFI, MEL, FER, MOR, clinoptilolite, MWW, TON, EUO, MFS and ZSM-48 (or $H^+$ or $NR_4^+$-form MFI, MEL, FER, MOR, clinoptilolite, MWW, TON, EUO, MFS and ZSM-48) has an initial atomic ratio Si/Al of 100 or lower and from 4 to 30 in a specific embodiment. The conversion to the $H^+$ or $NR_4^+$-form is known per se and is described in U.S. Pat. No. 3,911,041 and U.S. Pat. No. 5,573,990.

Advantageously the final P-content is at least 0.05 wt % and preferably between 0.3 and 7 w %. Advantageously at least 10% of Al, in respect to parent zeolite MFI, MEL, FER, MOR and clinoptilolite, MWW, TON, EUO, MFS and ZSM-48, have been extracted and removed from the zeolite by the leaching.

Then the zeolite either is separated from the washing solution or is dried without separation from the washing solution. Said separation is advantageously made by filtration. Then the zeolite is calcined, by way of example, at 400° C. for 2-10 hours.

In the steam treatment step, the temperature is preferably from 420 to 870° C., more preferably from 480 to 760° C. The pressure is preferably atmospheric pressure and the water partial pressure may range from 10 to 100 kPa. The steam atmosphere preferably contains from 5 to 100 vol % steam with from 0 to 95 vol % of an inert gas, preferably nitrogen. The steam treatment is preferably carried out for a period of from 0.01 to 200 hours, advantageously from 0.05 to 200 hours, more preferably from 0.05 to 50 hours. The steam treatment tends to reduce the amount of tetrahedral aluminium in the crystalline silicate framework by forming alumina.

The leaching can be made with an organic acid such as citric acid, formic acid, oxalic acid, tartaric acid, malonic acid, succinic acid, glutaric acid, adipic acid, maleic acid, phthalic acid, isophthalic acid, fumaric acid, nitrilotriacetic acid, hydroxyethylenediaminetriacetic acid, ethylenediaminetetracetic acid, trichloroacetic acid trifluoroacetic acid or a salt of such an acid (e.g. the sodium salt) or a mixture of two or more of such acids or salts. The other inorganic acids may comprise an inorganic acid such as nitric acid, hydrochloric acid, methansulfuric acid, phosphoric acid, phosphonic acid, sulfuric acid or a salt of such an acid (e.g. the sodium or ammonium salts) or a mixture of two or more of such acids or salts.

The residual P-content is adjusted by P-concentration in the aqueous acid solution containing the source of P, drying conditions and a washing procedure if any. A drying step can be envisaged between filtering and washing steps.

Said P-modified zeolite can be used as itself as a catalyst. In another embodiment it can be formulated into a catalyst by combining with other materials that provide additional hardness or catalytic activity to the finished catalyst product. Materials which can be blended with the P-modified zeolite can be various inert or catalytically active materials, or various binder materials. These materials include compositions such as kaolin and other clays, various forms of rare earth metals, phosphates, alumina or alumina sol, titania, zirconia, quartz, silica or silica sol, and mixtures thereof. These components are effective in densifying the catalyst and increasing the strength of the formulated catalyst. The catalyst may be formulated into pellets, spheres, extruded into other shapes, or formed into a spray-dried particles. The amount of P-modified zeolite which is contained in the final catalyst product ranges from 10 to 90 weight percent of the total catalyst, preferably 20 to 70 weight percent of the total catalyst.

Final equilibration step is performed advantageously at the temperature 400-800° C. in presence of steam for 0.01-48 h. Advantageously the steam partial pressure is at least 0.1 bars. Air, nitrogen or any inert gases can be fed together with steam.

A dehydration catalyst has already been described in WO2009098262.

Another family of suitable catalysts for the dehydration are alumina's as such, silica-alumina's or alumina's including γ-alumina, transitional aluminas such as α-alumina, β-alumina, γ-alumina, δ-alumina, ε-alumina, κ-alumina, ρ-alumina and alumina's that have been modified, by way of example, by surface treatment with silicon, lanthanum, chromium, phosphorous, zirconium, boron, tungsten, titanium or fluor.

Alumina's are generally characterised by a rather broad acid strength distribution and having both Lewis-type and Bronsted-type acid sites. The presence of a broad acid strength distribution makes the catalysis of several reactions, requiring each a different acid strength, possible. This often results in low selectivity for the desired product. Deposition of silicon, zirconium, boron, tungsten, lanthanum, chromium, phosphorous, titanium or fluor on the surface of alumina allows rendering the catalyst significantly more selective and improving the thermal and hydrothermal stability.

For the preparation of the alumina based catalyst, suitable commercial alumina's can be used, preferably eta or gamma alumina, having a surface area of 10 to 500 m2/gram and an alkali content of less than 0.5%. The catalyst according to the present invention is prepared by adding 0.05 to 10% of silicon, zirconium, titanium, zirconium, boron, tungsten, lanthanum, chromium, phosphorous. The addition of these elements can be done during the preparation of the alumina or can be added to the existing alumina, eventually already activated. Addition of the element during the preparation of the alumina can be done by dissolving the metal precursor together with the aluminium precursor before precipitation of the final alumina or by addition of the metal precursor to the aluminium hydroxide gel. A preferred method is adding metal precursors to the shaped alumina. Metal precursors are dissolved in a suitable solvent, either aqueous or organic, and contacted with the alumina by incipient wetness impregnation or by wet impregnation or by contacting with an excess of solute during a given time, followed by removing the excess solute. The alumina can also be contacted with vapour of the metal precursor. Suitable metal precursors are halides of silicon, zirconium, phosphorous, chromium, lantanium or titanium, oxyhalides or oxynitrates of zirconium or titanium; alcoxides of silicon, zirconium, boron or titanium; oxalates or citrates of zirconium or titanium, boric acid, nitrates of lantanium and chromium, phosphoric acid, ammonium phosphates, ammonium metatungstate etc. The solvent is selected according to the solubility of the metal precursor. The contacting can be done at temperature of 0° C. to 500° C., most preferred from 10° C. to 200° C. After the contacting, the alumina is eventually washed, dried and finally calcined in other to enhance the surface reaction between the elements and the alumina and the removal of the metal precursor ligands. The use of modified alumina's for the dehydration is preferably done in the presence of water. The weight ratio of water to alcohol ranges from 1/25 to 3/1. Fluorinated alumina is known in itself and can be made according to the prior art.

As regards step d), the fractionation of said effluent of step c) removes a portion or all the water, unconverted alcohols, optionally the inert component, and optionally the whole or a part of the various hydrocarbons to get a stream (D) comprising essentially olefins and optionally the inert component. The fractionation is carried out by any means, they are known per se.

"to remove optionally the inert component" has to be understood as follows:
If there is no inert component introduced at step a) it is clear that said inert component is not present in the effluent of step c) and not present in stream (D);
If an inert component is introduced at step a) there is in fractionation of step d)
   an option to remove it, thereby said inert component is not present in stream (D) or
   to let it, thereby said inert component is present in stream (D).

As regards stream (D1) of step f), it may comprise any kind of olefin-containing hydrocarbon stream. (D1) may typically comprise from 10 to 100 wt % olefins and furthermore may be fed undiluted or diluted by a diluent, the diluent optionally including a non-olefinic hydrocarbon. In particular, (D1) may be a hydrocarbon mixture containing normal and branched olefins in the carbon range $C_4$ to $C_{10}$, more preferably in the carbon range $C_4$ to $C_6$, optionally in a mixture with normal and branched paraffin's and/or aromatics in the carbon range $C_4$ to $C_{10}$. Typically, the olefin-containing stream has a boiling point of from around −15 to around 180° C.

In particularly preferred embodiments of the present invention, (D1) comprises $C_4$ mixtures from refineries and steam cracking units. Such steam cracking units crack a wide variety of feedstock's, including ethane, propane, butane, naphtha, gas oil, fuel oil, etc. Most particularly, (D1) may comprise a $C_4$ cut from a fluidized-bed catalytic cracking (FCC) unit in a crude oil refinery which is employed for converting heavy oil into gasoline and lighter products. Typically, such a $C_4$ cut from an FCC unit comprises around 30-70 wt % olefin. Alternatively, (D1) may comprise a $C_4$ cut from a unit within a crude oil refinery for producing methyl tert-butyl ether (MTBE) or ethyl tert-butyl ether (ETBE) which is prepared from methanol or ethanol and isobutene. Again, such a $C_4$ cut from the MTBE/ETBE unit typically comprises around 50 wt % olefin. These $C_4$ cuts are fractionated at the outlet of the respective FCC or MTBE/ETBE unit. (D1) may yet further comprise a $C_4$ cut from a naphtha steam-cracking unit of a petrochemical plant in which naphtha, comprising $C_5$ to $C_9$ species having a boiling point range of from about 15 to 180° C., is steam cracked to produce, inter alia, a $C_4$ cut. Such a $C_4$ cut typically comprises, by weight, 40 to 50% 1,3-butadiene, around 25% isobutylene, around 15% butene (in the form of but-1-ene and/or but-2-ene) and around 10% n-butane and/or isobutane. (D1) may also comprise a $C_4$ cut from a steam cracking unit after butadiene extraction (raffinate 1), or after butadiene hydrogenation, cracked naphtha, C4 ex MTO, FT (Fisher Tropsh) naphtha. MTO means a process which converts methanol, dimethyl ether or other oxygenates to olefins, said MTO process produces also C4 olefins.

(D1) may yet further alternatively comprise a hydrogenated butadiene-rich $C_4$ cut, typically containing greater than 50 wt % $C_4$ as an olefin. Alternatively, (D1) could comprise a pure olefin feedstock which has been produced in a petrochemical plant.

(D1) may yet further alternatively comprise light cracked naphtha (LCN) (otherwise known as light catalytic cracked spirit (LCCS)) or a $C_5$ cut from a steam cracker or light cracked naphtha, the light cracked naphtha being fractionated from the effluent of the FCC unit, discussed hereinabove, in a crude oil refinery. Both such feedstocks contain olefins. (D1) may yet further alternatively comprise a medium cracked naphtha from such an FCC unit or visbroken naphtha obtained from a visbreaking unit for treating the residue of a vacuum distillation unit in a crude oil refinery.

Advantageously the mixture of (D) and (D1) contains at least 20% of C4+ olefins.

Advantageously the mixture of (D) and (D1) contains least 1 wt % of C4 olefins providing form dehydration zone.

As regards the reaction in step f), it is referred as an "OCP process". It can be any catalyst provided it is selective to light olefins. Said OCP process is known per se. It has been described in EP 1036133, EP 1035915, EP 1036134, EP 1036135, EP 1036136, EP 1036138, EP 1036137, EP 1036139, EP 1194502, EP 1190015, EP 1194500 and EP 1363983 the content of which are incorporated in the present invention.

The catalysts used in low & high temperature zones can be the same or different.

The catalyst can be selected among the catalysts (A1) of step b) above and is employed under particular reaction conditions whereby the catalytic cracking of the $C_4^+$ olefins readily proceeds. Different reaction pathways can occur on the catalyst. Olefinic catalytic cracking may be understood to comprise a process yielding shorter molecules via bond breakage.

Should the water is not removed or should a substantial amount of water remains in the feed of step f) it is recommended to use in said OCP reactor a catalyst able to operate in the presence of water. Advantageously said catalyst is a P-modified zeolite as explained above in the description of the catalyst (A1).

In the catalytic cracking process of the OCP reactor, the process conditions are selected in order to provide high selectivity towards propylene or ethylene, as desired, a stable olefin conversion over time, and a stable olefinic product distribution in the effluent. Such objectives are favoured with a low pressure, a high inlet temperature and a short contact time, all of which process parameters are interrelated and provide an overall cumulative effect.

The process conditions are selected to disfavour hydrogen transfer reactions leading to the formation of paraffin's, aromatics and coke precursors. The process operating conditions thus employ a high space velocity, a low pressure and a high reaction temperature. The LHSV ranges from 0.5 to 30 hr$^{-1}$, preferably from 1 to 30 hr$^{-1}$. The olefin partial pressure ranges from 0.1 to 2 bars, preferably from 0.5 to 1.5 bars (absolute pressures referred to herein). A particularly preferred olefin partial pressure is atmospheric pressure (i.e. 1 bar). The mixture of (D) and optionally (D1) is preferably fed at a total inlet pressure sufficient to convey the feedstocks through the reactor. Said feedstock (the mixture of (D) and optionally (D1)) may be fed undiluted or diluted in an inert gas, e.g. nitrogen or steam. Preferably, the total absolute pressure in the reactor ranges from 0.5 to 10 bars. The use of a low olefin partial pressure, for example atmospheric pressure, tends to lower the incidence of hydrogen transfer reactions in the cracking process, which in turn reduces the potential for coke formation which tends to reduce catalyst stability. The cracking of the olefins is preferably performed at an inlet temperature of the feedstock of from 400° to 650° C., more preferably from 450° to 600° C., yet more preferably from 540° C. to 590° C. In order to maximize the amount of ethylene and propylene and to minimize the production of methane, aromatics and coke, it is desired to minimize the presence of diolefins in the feed. Diolefin conversion to monoolefin hydrocarbons may be accomplished with a conventional selective hydrogenation process such as disclosed in U.S. Pat. No. 4,695,560 hereby incorporated by reference.

The OCP reactor can be a fixed bed reactor, a moving bed reactor or a fluidized bed reactor. A typical fluid bed reactor is one of the FCC type used for fluidized-bed catalytic cracking in the oil refinery. A typical moving bed reactor is of the continuous catalytic reforming type. As described above, the process may be performed continuously using a pair of parallel "swing" reactors. The mixture of (D) and (D1) cracking process is endothermic; therefore, the reactor should be adapted to supply heat as necessary to maintain a suitable reaction temperature. Several reactors may be used in series with interheating between the reactors in order to supply the required heat to the reaction. Each reactor does a part of the conversion of the feedstock. Online or periodic regeneration of the catalyst may be provided by any suitable means known in the art.

The various preferred catalysts of the OCP reactor have been found to exhibit high stability, in particular being capable of giving a stable propylene yield over several days, e.g. up to ten days. This enables the olefin cracking process to be performed continuously in two parallel "swing" reactors wherein when one reactor is in operation, the other reactor is undergoing catalyst regeneration. The catalyst can be regenerated several times.

As regards step g) and the effluent of OCP reactor of step f), said effluent comprises methane, ethylene, propylene, optionally the inert component and hydrocarbons having 4 carbon atoms or more. Advantageously said OCP reactor effluent is sent to a fractionator and the light olefins (ethylene and propylene) are recovered. Advantageously the hydrocarbons having 4 carbon atoms or more are recycled at the inlet of the OCP reactor. Advantageously, before recycling said hydrocarbons having 4 carbon atoms or more at the inlet of the OCP reactor, said hydrocarbons having 4 carbon atoms or more are sent to a second fractionator to purge the heavies.

Optionally, in order to adjust the propylene to ethylene ratio, ethylene in whole or in part can be recycled over the OCP reactor and advantageously converted into more propylene. Ethylene can also be recycled in whole or in part at the inlet of the reactor (A).

One skilled in the art will also appreciate that the olefin products made by the present invention can be polymerized, optionally with comonomers, to form polyolefins, particularly polyethylenes and polypropylenes.

EXAMPLES

Experimental

The stainless-steel reactor tube has an internal diameter of 10 mm. 10 ml of catalyst, as pellets of 35-45 mesh, is loaded in the tubular reactor. The void spaces before and after the catalyst are filled with SiC granulates of 2 mm. The temperature profile is monitored with the aid of a thermocouple well placed inside the reactor. The reactor temperature is increased at a rate of 60° C./h to 550° C. under air, kept 2 hours at 550° C. and then purged by nitrogen. The nitrogen is then replaced by the feed at the indicated operating conditions. The catalytic tests are performed down-flow, in a pressure range of 1.5-2.0 bara, in a temperature range of 280-380° C. and with a weight hour space velocity (WHSV) varying from 7 to 21 h$^{-1}$.

Analysis of the products is performed by using an on-line gas chromatography.

Example 1

The catalyst used here is a crystalline silicate of the FER structure. The H-FER has a Si/Al of 33 under powder form. The catalyst is calcinated with air at 550° C. during 4 hours before formulation in pellets of 35-45 mesh.

An isobutanol/water mixture having the 95/5 wt % composition has been processed on the catalyst under 2 bara, at temperatures between 350 and 375° C., and with an isobutanol space velocity from 7 to 21 h$^{-1}$. The results are given in the table 1 on CH2-basis and coke free basis.

In this set of operating conditions, isobutanol conversion is almost complete, with a butenes selectivity of over 95% wt, and an olefin's selectivity close to 100%.

TABLE 1

| FEED | iButOH/H2O (95/5) % wt | | | | |
|---|---|---|---|---|---|
| P (bara) | 2 | 2 | 2 | 2 | 2 |
| T (° C.) | 350.0 | 350.0 | 350.0 | 375.0 | 375.0 |
| WHSV (H-1) | 7.3 | 12.6 | 21.0 | 21.0 | 12.6 |
| conversion (% wt CH2) | 100.0 | 99.4 | 89.7 | 99.8 | 99.2 |
| Oxygenates on C-basis (% wt CH2)—average | | | | | |
| Ether | 0.0 | 0.0 | 0.0 | 0.0 | 0.0 |
| Other alcohol | 0.1 | 0.1 | 0.2 | 0.1 | 0.1 |
| Aldehyde + Ketone | 0.1 | 0.1 | 0.1 | 0.1 | 0.1 |
| Yield on C-basis (% wt CH2)—average | | | | | |
| Paraffins | 1.0 | 0.4 | 0.2 | 0.4 | 0.4 |
| C2= | 0.8 | 0.5 | 0.3 | 0.7 | 0.4 |
| C3= | 0.2 | 0.1 | 0.0 | 0.1 | 0.1 |
| C4= | 95.9 | 97.4 | 88.7 | 97.8 | 97.5 |
| C5+ olef | 1.4 | 0.6 | 0.3 | 0.5 | 0.5 |
| Dienes | 0.4 | 0.2 | 0.0 | 0.1 | 0.1 |
| Aromatics | 0.1 | 0.0 | 0.0 | 0.0 | 0.0 |
| Unknown | 0.1 | 0.0 | 0.0 | 0.0 | 0.0 |
| Selectivity on C-basis (% wt CH2)—average | | | | | |
| Paraffins | 1.0 | 0.4 | 0.2 | 0.4 | 0.4 |
| C2= | 0.8 | 0.5 | 0.3 | 0.7 | 0.4 |
| C3= | 0.2 | 0.1 | 0.0 | 0.1 | 0.1 |

TABLE 1-continued

| FEED | iButOH/H2O (95/5) % wt | | | | |
|---|---|---|---|---|---|
| C4= | 95.9 | 98.0 | 98.8 | 97.9 | 98.3 |
| C5+ olef | 1.4 | 0.6 | 0.3 | 0.5 | 0.5 |
| Dienes | 0.4 | 0.2 | 0.0 | 0.1 | 0.1 |
| Aromatics | 0.1 | 0.0 | 0.0 | 0.0 | 0.0 |
| Unknown | 0.1 | 0.0 | 0.0 | 0.0 | 0.0 |
| C4 = distribution (% wt CH2) | | | | | |
| i-C4= | 43.4 | 42.2 | 42.4 | 42.2 | 41.6 |
| n-C4= | 56.6 | 57.8 | 57.6 | 57.8 | 58.4 |
| t-2-C4= | 27.0 | 27.7 | 27.9 | 27.0 | 28.0 |
| c-2-C4- | 18.4 | 18.7 | 18.6 | 18.7 | 18.9 |
| 1-C4= | 11.2 | 11.4 | 11.1 | 12.1 | 11.5 |

Example 2

The catalyst is cylinder-shaped gamma-alumina from Sasol® formulated. The catalyst has a specific surface are of 182 m²/g and a porous volume of 0.481 ml/g. The impurities present on the alumina in small amount are summarized below: 0.25% wt Si, 0.02% wt P, 0.02% wt fe, 29 ppm Na.

An isobutanol/water mixture having the 95/5 wt % composition has been processed on the catalyst under 2 bara, at temperatures between 350 and 380° C., and with an isobutanol space velocity from 7 to 12 h$^{-1}$. The results are given in the table 2 on CH2-basis and coke free basis.

In this set of operating conditions, isobutanol conversion is almost complete, with a butenes selectivity of over 98% wt, and an olefin's selectivity close to 100%.

TABLE 2

| FEED | i-ButOH/H2O (95/5) % wt | | | |
|---|---|---|---|---|
| P (bara) | 2 | 2 | 2 | 2 |
| T (° C.) | 380.0 | 350.0 | 350.0 | 325.0 |
| WHSV (H-1) | 12.4 | 7.4 | 12.4 | 7.4 |
| Conversion (% wt CH2) | 99.98 | 99.96 | 99.93 | 99.85 |
| Oxygenates (% wt CH2)—average | | | | |
| Other Oxygenates | 0.0 | 0.0 | 0.0 | 0.0 |
| Other alcohol | 0.0 | 0.1 | 0.1 | 0.1 |
| Selectivity on C-basis (% wt CH2)—average | | | | |
| Paraffins | 0.3 | 0.3 | 0.1 | 0.3 |
| C2= | 0.3 | 0.2 | 0.2 | 0.1 |
| C3= | 0.2 | 0.1 | 0.0 | 0.0 |
| C4= | 98.2 | 98.6 | 99.1 | 98.6 |
| C5+ olef | 0.7 | 0.5 | 0.1 | 0.3 |
| Dienes | 0.1 | 0.0 | 0.0 | 0.1 |
| Aromatics | 0.0 | 0.0 | 0.0 | 0.0 |
| Unknown | 0.1 | 0.1 | 0.3 | 0.4 |
| C4 = distribution (% wt) | | | | |
| IC4= | 90.2 | 92.5 | 92.7 | 94.0 |
| t-2-C4= | 3.0 | 1.8 | 1.4 | 1.2 |
| c-2-C4- | 3.9 | 3.2 | 3.3 | 2.7 |
| 1-C4= | 2.9 | 2.5 | 2.6 | 2.1 |
| n-C4= | 9.8 | 7.5 | 7.3 | 6.0 |

Example 3

The catalyst is a phosphorous modified zeolite (P-ZSM5), prepared according to the following recipe. A sample of zeolite ZSM-5 (Si/Al=13) in H-form was steamed at 550° C. for 6 h in 100% H$_2$O. Then, 1270 g of the steamed solid was subjected to a contact with 241.3 g of an aqueous solution of H$_3$PO$_4$ (85% wt) for 2 h under reflux condition (4 ml/1 g zeolite) followed by addition of 69.9 g of CaCO3. Then the solution was dried by evaporation under rigours stirring for 3 days at 80° C. 750 g of the dried sample was extruded with 401.5 g of silica sol Bindzil (34 wt % SiO2), and 3 wt % of extrusion additives. The shaped sample contained about 80 wt % zeolite. The extruded solid was dried at 110° C. for 16 h and steamed at 600° C. for 2 h.

An isobutanol/water mixture having the 95/5 wt % composition has been processed on the catalyst under 1.5 bara, at temperatures between 280 and 350° C., and with an isobutanol space velocity of about 7 h$^{-1}$. The results are given in the table 3 on CH2-basis and coke free basis.

In this set of operating conditions, isobutanol conversion is almost complete, with a butenes selectivity of over 90% wt, and total olefin's selectivity close to 100%.

TABLE 3

| FEED : i-ButOH/H2O (95/5) % wt | | |
|---|---|---|
| P (bara) | 1.5 | 1.5 |
| T (° C.) | 300 | 280 |
| WHSV (H-1) | 7.4 | 7.4 |
| Conversion (% wt CH2) | 100.0 | 83.5 |
| Oxygenates (% wt CH2)—Average | | |
| Other alcohols | 0.01 | 0.00 |
| Other Oxygenates | 0.03 | 0.08 |
| Selectivity on C-basis (% wt CH2)—Average | | |
| Paraffins C1-C4 | 0.1 | 0.1 |
| C2= | 0.0 | 0.0 |
| C3= | 0.5 | 0.3 |
| C4= | 89.9 | 93.9 |
| 1-Butene | 60.3 | 61.9 |
| 1-Butene | 5.0 | 6.1 |
| 2-Butene | 24.6 | 26.0 |
| C5+ olef | 4.8 | 2.7 |
| C5+ paraf | 1.9 | 1.1 |
| Dienes | 0.5 | 0.4 |
| Aromatics | 0.5 | 0.2 |
| Unknown | 1.6 | 1.1 |
| C4 = distribution—Average | | |
| i-Butene | 67.1 | 65.9 |
| n-butenes | 32.9 | 34.1 |
| 1-Butene | 5.5 | 6.5 |
| 2-Butene | 27.4 | 27.7 |

These examples illustrate a possibility to transform i-butanol into olefinic feedstock which can be further converted in OCP to ethylene and propylene.

OCP Reactor: the butenes from dehydration are mixed with a refinery stream to get a mixture (D+D1) comprising about 60 w % olefins.

The catalyst is a phosphorous modified zeolite (P-ZSM5), prepared according to the following recipe. A sample of zeolite ZSM-5 (Si/Al=13) in H-form was steamed at 550° C. for 6 h in 100% H$_2$O. Then, 600 g of the steamed solid was subjected to a contact with 114 g of an aqueous solution of H$_3$PO$_4$ (85% wt) for 2 h under reflux condition (4 ml/1 g zeolite) followed by addition of 38 g of CaCO3. Then the solution was dried by evaporation under rigours stirring for 3 days at 80° C. 534 g of the dried sample was extruded with 315 g of silica sol Bindzil (34 wt % SiO2), 107.1 g of precipitated silica (H-5, Cabot) and 3 wt % of extrusion additives. The shaped sample contained about 70 wt % zeolite. The extruded solid was dried at 110° C. for 16 h and steamed at 600° C. for 2 h.

Catalyst tests were performed on 10 ml (5.6 g) of catalyst grains (35-45 meshes) loaded in the tubular reactor. The feedstock C4 which contains substantially non cyclic olefins C4

(~60 wt %) was subjected to catalytic cracking in the presence of catalyst in a fixed bed reactor at 570° C., WHSV=10 h$^{-1}$, P=1.5 bara. FIG. depicts a catalyst stability of P-ZSM-5 in olefins cracking.

The invention claimed is:
1. A process comprising:
 a) introducing in a reactor (A) a stream comprising about 20 weight percent to 100 weight percent isobutanol, optionally water, optionally an inert component;
 b) contacting said stream with a catalyst (A1) in said reactor (A) at conditions effective to dehydrate the isobutanol to butenes;
 c) recovering from said reactor (A) an effluent comprising substantially butenes, optionally olefins other than butene, water, optionally unconverted alcohols, and optionally the inert component of step a);
 d) fractionating said effluent of step c) to remove a portion or all the water, optionally unconverted alcohols, optionally the inert component to get a stream (D) comprising butenes and optionally the inert component;
 e) introducing a feedstock comprising at least a part of said stream (D) in an OCP reactor;
 f) contacting said feedstock comprising said stream (D), optionally in combination with a stream (D1) comprising olefins having 4 carbon atoms or more, in said OCP reactor with a P-modified zeolite catalyst which is selective towards light olefins in the effluent, to produce an effluent with an olefin content of lower molecular weight than that of the feedstock;
 g) fractionating said effluent of step f) to produce at least an ethylene stream, a propylene stream and a fraction consisting essentially of hydrocarbons having 4 carbon atoms or more, optionally recycling the ethylene in whole or in part at an inlet of the OCP reactor of step f), or at an inlet of the reactor (A) or at the inlet of both the OCP reactor of step f) and the reactor (A), optionally recycling the fraction consisting essentially of hydrocarbons having 4 carbon atoms or more at the inlet of the OCP reactor;
 wherein a process for preparing the P-modified zeolite comprises the following sequential steps:
  selecting a zeolite among H$^+$-form and NH4$^+$-form of MFI, MEL, FER, MOR, clinoptilolite, MWW, TON, EUO, MFS and ZSM-48, wherein the selected zeolite has an initial Si/Al ratio between 4 and 500;
  steaming the zeolite at a temperature ranging from 400 to 870° C. for 0.01 to 200 hours;
  leaching the zeolite in an aqueous acid solution containing a source of P at conditions to remove Al from the zeolite and to introduce at least 0.05 wt % of P;
  separating solid zeolite from liquid, if any; and
  calcination of the zeolite.
2. The process of claim 1, wherein the selected zeolite has an initial Si/Al ratio between 4 to 30.

3. The process of claim 1, wherein the zeolite is selected among H$^+$-form and NH4$^+$-form of silicalite-1, boralite C, TS-1, MEL, FER, MOR, clinoptilolite, MWW, TON, EUO, MFS and ZSM-48.

4. The process of claim 1, wherein the zeolite is selected among H$^+$-form and NH4$^+$-form of MEL, FER, MOR, clinoptilolite, MWW, TON, EUO, MFS and ZSM-48.

5. The process of claim 1, wherein the crystalline silicate is an FER, MWW, TON, EUO, MFS or ZSM-48.

6. The process of claim 1, wherein:
 the steam introduced in the reactor (A) at step a) comprises about 60 weight percent to 100 weight percent isobutanol.

7. The process of claim 1, wherein the catalyst (A1) is a porous crystalline aluminophosphate.

8. The process of claim 7, wherein the porous crystalline aluminophosphate is substituted with silicon, boron, Ni, Zn, Mg, or Mn.

9. The process of claim 7, wherein the porous crystalline aluminophosphate is an AEL, AFI, AFO or FAU.

10. The process of claim 7, wherein the porous crystalline aluminophosphate is porous crystalline silicoaluminophosphate (SAPO).

11. The process of claim 1, wherein the catalyst (A1) is a crystalline silicate.

12. The process of claim 11, wherein the crystalline silicate is an MFI, MEL, FER, MTT, MWW, TON, EUO, MFS or ZSM-48.

13. The process of claim 11, wherein the crystalline silicate a dealuminated crystalline silicate.

14. The process of claim 11, wherein the crystalline silicate has a ratio Si/Al of at least 10.

15. The process of claim 11, wherein the crystalline silicate has a ratio Si/Al of at least 100.

16. The process of claim 11, wherein the crystalline silicate is essentially in H-form.

17. The process of claim 1, wherein the catalyst (A1) is an alumina.

18. The process of claim 17, wherein the alumina is a silica-alumina.

19. The process of claim 17, wherein the alumina is a γ-alumina, α-alumina, β-alumina, δ-alumina, ε-alumina, κ-alumina, p-alumina.

20. The process of claim 17, wherein the alumina is modified by surface treatment with silicon, lanthanum, chromium, phosphorous, zirconium, boron, tungsten, titanium or fluor.

21. The process of claim 1, wherein the catalyst (A1) and the catalyst in the OCP reactor of step f) are the different.

22. The process of claim 1, wherein the contacting of said stream with the catalyst (A1) in said reactor (A) is at conditions effective to dehydrate the isobutanol to essentially butenes with a butenes selectivity of over 90 weight percent, and wherein a temperature in the reactor (A) ranges from 280° C. to 450° C.

* * * * *